US00PP16270P2

(12) United States Plant Patent
Clevenger

(10) Patent No.: US PP16,270 P2
(45) Date of Patent: Feb. 21, 2006

(54) APPLE TREE NAMED 'FUGACHEE FUJI'

(50) Latin Name: *Malus pumila*
Varietal Denomination: Fugachee Fuji

(76) Inventor: Ira Clevenger, 885 Seamist #207, Ventura, CA (US) 93003

( * ) Notice: Subject to any disclaimer, the term of this patent is extended or adjusted under 35 U.S.C. 154(b) by 127 days.

(21) Appl. No.: 10/713,611

(22) Filed: Nov. 13, 2003

Related U.S. Application Data

(60) Provisional application No. 60/426,974, filed on Nov. 15, 2002.

(51) Int. Cl.
*A01H 5/00* (2006.01)

(52) U.S. Cl. ..... Plt./168

(58) Field of Classification Search ..... Plt./168, Plt./161
See application file for complete search history.

(56) References Cited

U.S. PATENT DOCUMENTS

PP11,193 P * 1/2000 Van Leuven ..... Plt./168

* cited by examiner

*Primary Examiner*—Bruce R. Campell
*Assistant Examiner*—Susan B. McCormick-Ewoldt
(74) *Attorney, Agent, or Firm*—Stratton Ballew PLLC

(57) ABSTRACT

A new and distinct variety of Fuji apple tree (*Malus pumila*) named 'Fugachee Fuji' is disclosed. The fruit of the new variety is characterized by its early maturity and attractive blush coloration.

6 Drawing Sheets

Latin name of the genus and species of the plant claimed: *Malus pumila.*
Variety denomination: 'Fugachee Fuji'.

BACKGROUND OF THE INVENTION

The 'Fugachee Fuji' apple tree was discovered as a sport mutation of its parent 'Fuji' (unpatented) tree in a cultivated orchard near Brewster, Wash. in 1998. 'Fugachee Fuji' was asexually propagated by budding at the same location in 1998, and has been observed to remain stable and true to type over successive generations.

BRIEF SUMMARY OF THE INVENTION

The 'Fugachee Fuji' apple tree is distinguishable from its parent 'Fuji' and from other known and related varieties by its early maturing fruit, and fruit coloration having a pronounced blush covering seventy to 90 percent of the fruit surface. Fruit of 'Fugachee Fuji' is further distinguishable by its large size as compared to 'Fuji'.

'Fugachee Fuji' has been compared to 'Fiero' (U.S. Plant Pat. No. 11,193), a similar 'Fuji'-type apple tree. Like 'Fiero', 'Fugachee Fuji' is an early maturing variety, and its fruit exhibits an attractive blush overcolor. However, 'Fugachee Fuji' matures even earlier than 'Fiero'. A comparison of 'Fugachee Fuji', 'Fuji' and 'Fiero' is shown in Table 1:

TABLE 1

Comparison of 'Fugachee Fuji' to 'Fuji' and 'Fiero'

| | 'Fugachee Fuji' | 'Fuji' | 'Fiero' |
|---|---|---|---|
| Maturity Date | Late September | Late October | Mid October |
| Color | 70–90% red blush | 25–50% red blush or stripe | 60–100% red blush |

BRIEF DESCRIPTION OF THE PHOTOGRAPHS

Figure 1:
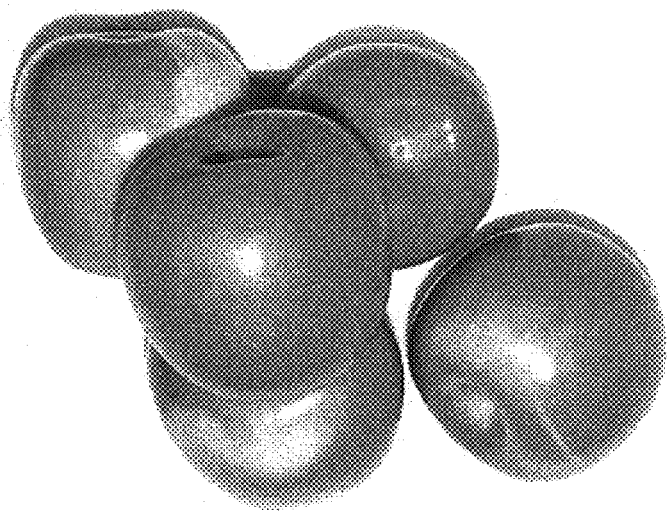
Figure 2:
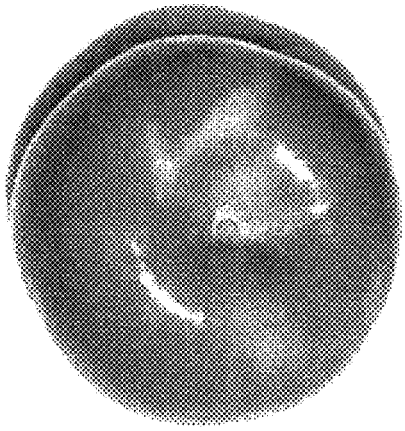
Figure 3:
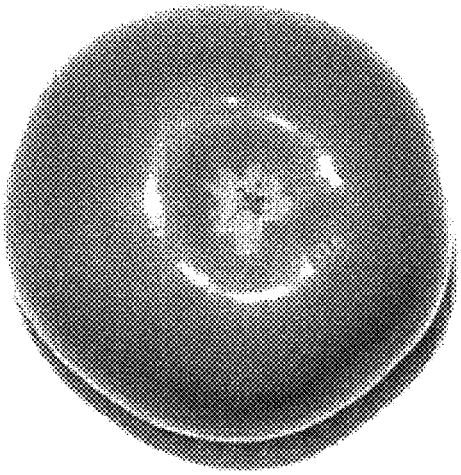
Figure 4:
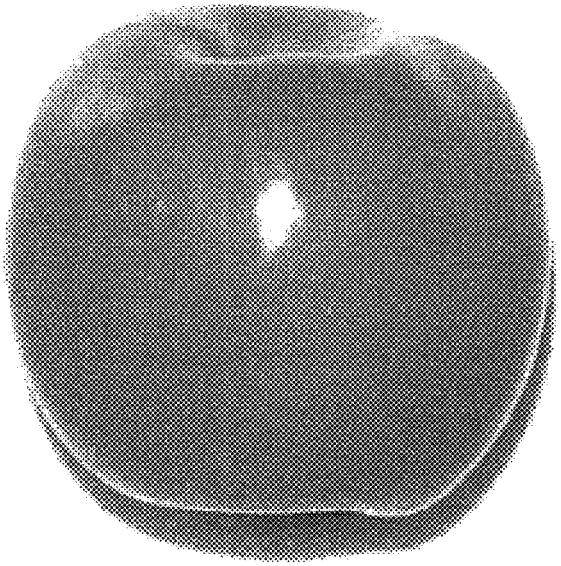
Figure 5:
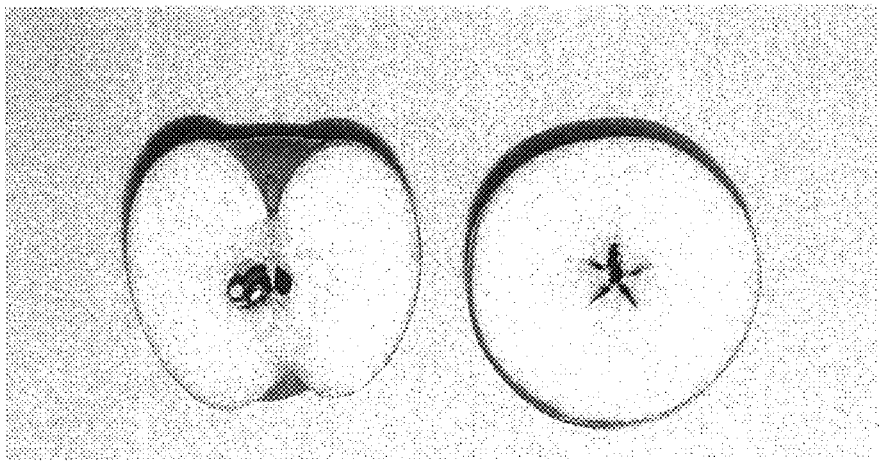
Figure 6:
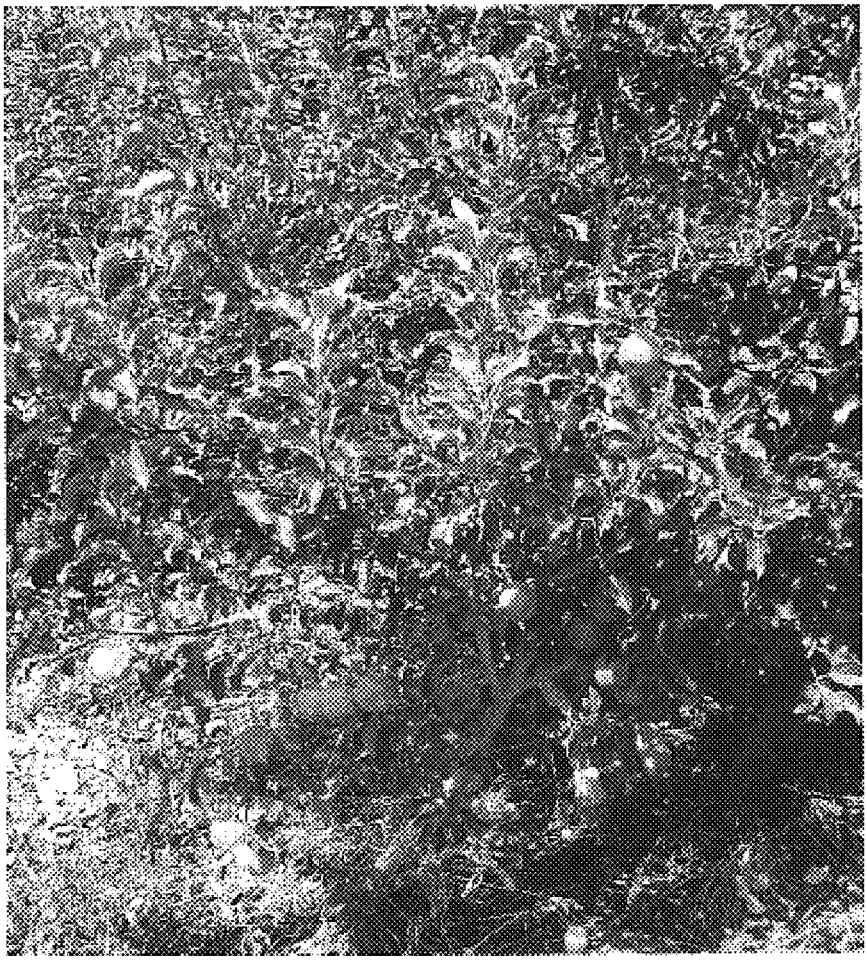

FIG. 1 shows a selection of fruit of 'Fugachee Fuji';
FIG. 2 shows a fruit of 'Fugachee Fuji';
FIG. 3 shows a fruit of 'Fugachee Fuji';
FIG. 4 shows a fruit of 'Fugachee Fuji';
FIG. 5 shows sectioned fruit of 'Fugachee Fuji'; and
FIG. 6 shows a 'Fugachee Fuji' tree and leaves.

DETAILED BOTANICAL DESCRIPTION OF THE VARIETY

The following detailed botanical description of 'Fugachee Fuji' is based on observations made during the 2003 and 2004 growing seasons of trees planted in 2002 at Brewster, Wash. and Parker, Wash., USA. Colors, except those colors described in common terms, are set forth in accordance with The Royal Horticultural Society Colour Chart (2001). The botanical characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:
*Vigor.*—Vigorous.
*Type.*—Non-Spur.
*Habit.*—Spreading.
*Size.*—Height, 1.5 m; diameter, 2.7 m.
*Trunk.*—Diameter 20 cm at 10 cm above graft union; bark texture rough; brown N200D, greyed-orange173B, greyed-orange165A; smooth areas greyed-orange 166A; lenticels 0.2 to 0.8 cm long; lenticel color greyed orange 165D.

*Branches.*—Length 120 cm; diameter 4 cm; smooth; greyed-orange 165A; internode length 4 to 6 cm.

*Winter hardiness.*—Hardy where tested (Brewster, Wash.).

Flowers:

*Bud.*—Quantity per spur 4 to 6; elongated; length 0.9 cm; diameter 0.6 cm; yellow-green 146C; tip red-purple 62A.

*Flower color* (*balloon stage*).—White 155D.

*Flower size.*—Diameter 4.3 to 4.4 cm; 4 to 6 flowers per cluster; not showy.

*Petals.*—5 per flower; overlapping; length 1.7 cm; width 1.1 cm; margin smooth; upper surface color white 155D; lower surface color white 155D when fully open.

*Sepals.*—Length 4 mm; width 2 mm; yellow-green 146C.

*Pistil.*—Quantity 5; length 8 to 10 mm; yellow-green 145C.

*Anthers.*—Length 5 mm; pollen abundant, yellow 1A.

*Bloom period.*—March 28 to April 20 at Brewster, Wash.

Leaf:

*Leaf size.*—Length 9 cm; width 6 cm.

*Length-width ratio.*—Medium.

*Margin.*—Serrate.

*Shape.*—Ovate; base rounded; apex acute.

*Venation.*—Reticulate.

*Color.*—Upper surface green 137A; lower surface green 138D; vein green 138D.

*Petiole.*—Length 4.5 cm; diameter 1 mm; yellow green 145B.

Fruit:

*Size.*—Diameter 8.0 cm; height 8 1 cm.

*Ratio of height to width.*—Medium.

*General shape in profile.*—Globose.

*Position of maximum diameter.*—Middle.

*Crowning at calyx end.*—Absent or very weak.

*Depth of eye basin.*—0.6 cm.

*Width of eye basin.*—2.9 cm.

*Stalk.*—Length 3.0 cm, width 0.4 cm at limb attachment; Yellow 1C.

*Depth of stalk cavity.*—2.0 cm.

*Width of stalk cavity.*—4.1 cm.

*Size of lenticels.*—Small; diameter approximately 1.0 mm.

*Bloom of skin.*—Present.

*Ground color of skin.*—Yellow green 151C.

*Over color of skin.*—Red N34D.

*Amount of over color.*—70% to 90%.

*Intensity of over color.*—Medium.

*Pattern of over color.*—Solid flush.

*Skin thickness.*—Medium.

*Skin texture.*—Smooth.

*Flesh.*—White 158A, slightly astringent, slightly tart, firm, crisp, very juicy.

*Seeds.*—Avg. 6 per fruit; width 0.5 cm; length 1.0 cm; greyed-orange 165A, oval, smooth.

*Quantity per cluster.*—Avg 3 to 5.

Use: Fresh market.

Resistance to known diseases: None noted.

Storageability: Not yet evaluated.

What is claimed is:

1. A new and distinct apple tree substantially as shown and described herein.

* * * * *